US006399575B1

(12) United States Patent
Smith et al.

(10) Patent No.: US 6,399,575 B1
(45) Date of Patent: Jun. 4, 2002

(54) METHODS AND COMPOSITIONS FOR TARGETING COMPOUNDS TO THE CENTRAL NERVOUS SYSTEM

(75) Inventors: Bruce F. Smith; Tatiana I. Samoilova; Henry J. Baker, all of Auburn, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 09/438,150

(22) Filed: Nov. 10, 1999

Related U.S. Application Data

(60) Provisional application No. 60/108,418, filed on Nov. 10, 1998.

(51) Int. Cl.$^7$ .......................... A61K 38/08; C07K 7/06
(52) U.S. Cl. ......................................... 514/16; 530/329
(58) Field of Search ............................... 530/326–329; 514/13–16

(56) References Cited

U.S. PATENT DOCUMENTS

| 4,675,382 A | * | 6/1987 | Murphy |
| 5,432,155 A | * | 7/1995 | Olivera et al. |
| 5,622,699 A | | 4/1997 | Ruoslahti et al. |
| 5,650,267 A | * | 7/1997 | Ray et al. |

OTHER PUBLICATIONS

Rudinger, In *Peptide Hormones,* ed. J. A. Parsons, University Park Press, Baltimore, pp. 1–7, 1976.*
Miyasaka et al. *Eur. J. Biochem.,* vol. 216, pp. 343–352, 1993.*
Barry et al., Toward Cell–Targeting Gene Therapy Vectors: Selection of Cell–Binding Peptides From Random Peptide–Presenting Phage Libraries, Nature Medicine, 1996, pp. 299–305, vol. 2, No. 3.

Pasqualini et al., Organ Targeting In Vivo Using Phage Display Peptide Libraries, Nature, 1996, pp. 364–366, vol. 380.

Rajotte et al., Molecular Heterogeneity of the Vascular Endothelium Revealed by In Vivo Phage Display, J. Clin. Invest., 1998, pp. 430–437, vol. 102, No. 2.

Schumacher et al., Identification of D–Peptide Ligands Through Mirror–Image Phage Display, Science, 1996, pp. 1854–1857, vol. 271.

Abstract: 0–155, Polgren et al., Tumor Biology 18(Suppl.1) 77, 1997. Identification of Muscle Homing Sequences by Using Phage Display Libraries of Peptides.

* cited by examiner

*Primary Examiner*—Gary L. Kunz
*Assistant Examiner*—Stephen Gucker
(74) *Attorney, Agent, or Firm*—Alston & Bird LLP

(57) ABSTRACT

Compositions for use in targeting therapies to central nervous system (CNS) cells are provided. The compositions comprise peptides which are capable of binding CNS cells in vivo.

4 Claims, 3 Drawing Sheets

FIGURE 3

Amino acid sequence of muscle and brain binding peptide:

GETRAPL (Gly-Glu-Thr-Arg-Ala-Pro-Leu)

Amino acid sequences of brain specific peptides:

LPLTPLP (Leu-Pro-Leu-Thr-Pro-Leu-Pro)

SSHTISF (Ser-Ser-His-Thr-Ile-Ser-Phe)

LPHQNNR (Leu-Pro-His-Gln-Asn-Asn-Arg)

QPTASLT (Gln-Pro-Thr-Ala-Ser-Leu-Thr)

LFTPPVL (Leu-Phe-Thr-Pro-Pro-Val-Leu)

SEQUENCE LISTING

<160> NUMBER OF SEQ ID NOS: 6

<210> SEQ ID NO 1
<211> LENGTH: 7
<212> TYPE: PRT
<213> ORGANISM: Artificial Sequence
<220> FEATURE:
<223> OTHER INFORMATION: Phage display library peptides

<400> SEQUENCE: 1

Leu Pro Leu Thr Pro Leu Pro
 1               5

```
<210> SEQ ID NO 2
<211> LENGTH: 7
<212> TYPE: PRT
<213> ORGANISM: Artificial Sequence
<220> FEATURE:
<223> OTHER INFORMATION: Phage display library peptides

<400> SEQUENCE: 2

Ser Ser His Thr Ile Ser Phe
 1               5

<210> SEQ ID NO 3
<211> LENGTH: 7
<212> TYPE: PRT
<213> ORGANISM: Artificial Sequence
<220> FEATURE:
<223> OTHER INFORMATION: Phage display library peptides

<400> SEQUENCE: 3

Leu Pro His Gln Asn Asn Arg
 1               5

<210> SEQ ID NO 4
<211> LENGTH: 7
<212> TYPE: PRT
<213> ORGANISM: Artificial Sequence
<220> FEATURE:
<223> OTHER INFORMATION: Phage display library peptides

<400> SEQUENCE: 4

Gln Pro Thr Ala Ser Leu Thr
 1               5

<210> SEQ ID NO 5
<211> LENGTH: 7
<212> TYPE: PRT
<213> ORGANISM: Artificial Sequence
<220> FEATURE:
<223> OTHER INFORMATION: Phage display library peptides

<400> SEQUENCE: 5

Leu Phe Thr Pro Pro Val Leu
 1               5

<210> SEQ ID NO 6
<211> LENGTH: 7
<212> TYPE: PRT
<213> ORGANISM: Artificial Sequence
<220> FEATURE:
<223> OTHER INFORMATION: Phage display library peptides

<400> SEQUENCE: 6

Gly Glu Thr Arg Ala Pro Leu
 1               5
```

METHODS AND COMPOSITIONS FOR TARGETING COMPOUNDS TO THE CENTRAL NERVOUS SYSTEM

CROSS-REFERENCE TO RELATED APPLICATION

This application claims the benefit of U.S. Provisional Application No. 60/108,418, filed Nov. 10, 1998.

FIELD OF THE INVENTION

The invention relates to targeting methods for therapy; particularly for targeting genes, proteins, pharmaceuticals, or other compounds to the central nervous system.

BACKGROUND OF THE INVENTION

The capabilities to introduce a particular foreign or native gene sequence into a mammal and to control the expression of that gene are of substantial value in the fields of medical and biological research. Such capabilities provide a means for studying gene regulation and for designing a therapeutic basis for the treatment of disease.

In addition to introducing the gene into mammals, providing expression of the gene at the site of interest remains a challenge. Methods have been developed to deliver DNA to target cells by capitalizing on endogenous cellular pathways of macromolecular transport. In this regard, gene transfer has been accomplished via the receptor-mediated endocytosis pathway employing molecular conjugate vectors.

Inherited diseases of the central nervous system (CNS) pose a therapeutic challenge. Pharmacological approaches do not significantly alter the course of many of these diseases as such approaches fail to correct the underlying genetic deficit. New approaches, relying on the transfer of genetic material have been advocated. However, current methodologies used for gene therapy are limited in their usefulness with regard to treating CNS disorders.

A particular challenge to delivery of many substances to the CNS, including substances for gene therapy, is posed by the selective permeability of the Blood Brain Barrier (BBB). BBB is formed by cerebral endothelial cells and limits the passage of substances from blood into CNS cells, particularly large and/or highly polar molecules.

Under certain pathological conditions, including CNS lesions caused by infections, inflammatory conditions, neoplasms, and ischemia, the BBB becomes more permeable relative to normal conditions. This change in permeability has been used in designing a method for delivering drugs to the CNS in conjunction with substances that neutralize the excess drug circulating outside the BBB to minimize systemic side effects (U.S. Pat. No. 5,124,149).

Other approaches for delivering substances to the CNS have included circumventing the BBB by intrathecal administration into cerebrospinal fluid by direct injection or surgical implant, direct injection and infusion into CNS tissue (Ommaya et al. (1984) *Cancer Drug Delivery* 1(2):169–178; U.S. Pat. No. 5,222,982; Bobo et al. (1994) *Proc. Natl. Acad. Sci. USA* 91:2076–2080); altering the blood brain barrier by osmotic disruption through use of chemical agents (U.S. Pat. No. 4,866,042), use of carriers capable of crossing the BBB (U.S. Pat. No. 5,716,614), and tagging with molecules capable of binding specific CNS receptors (U.S. Pat. No. 5,527,527).

Direct administration of therapeutic substances to the CNS, particularly the brain, is rare and associated with high safety risk. Additionally, local administration of gene therapy vectors or transplantation of donor cells is likely to only treat the immediate area of the injection site. Effective therapy with these methods requires multiple injections and carry the safety risks associated with intrusion into the CNS, disease transmission and the use of immunosuppressive drugs.

Current approaches to gene therapy in inherited CNS disorders are limited in practicality by the mode of administration or the capacity of the vector used for gene transfer. Therefore, methods are needed for targeting specific compositions to CNS cells.

SUMMARY OF THE INVENTION

Compositions and methods for targeting genes, proteins, pharmaceuticals, or other compounds to the central nervous system (CNS) are provided. The compositions comprise peptide sequences which bind CNS tissue, in vivo, with high specificity.

The compositions are useful in therapy methods for the treatment of CNS disorders, and delivery of a wide variety of compounds to the CNS, including nucleotides, proteins and small molecule pharmaceuticals.

BRIEF DESCRIPTION OF THE DRAWINGS

FIG. 3 sets forth the amino acid sequences for a muscle and brain binding peptide (SEQ. ID NO:6, and the amino acid sequences of brain specific peptides(SEQ ID NOS: 1–5).

DETAILED DESCRIPTION OF THE INVENTION

Figure 1:
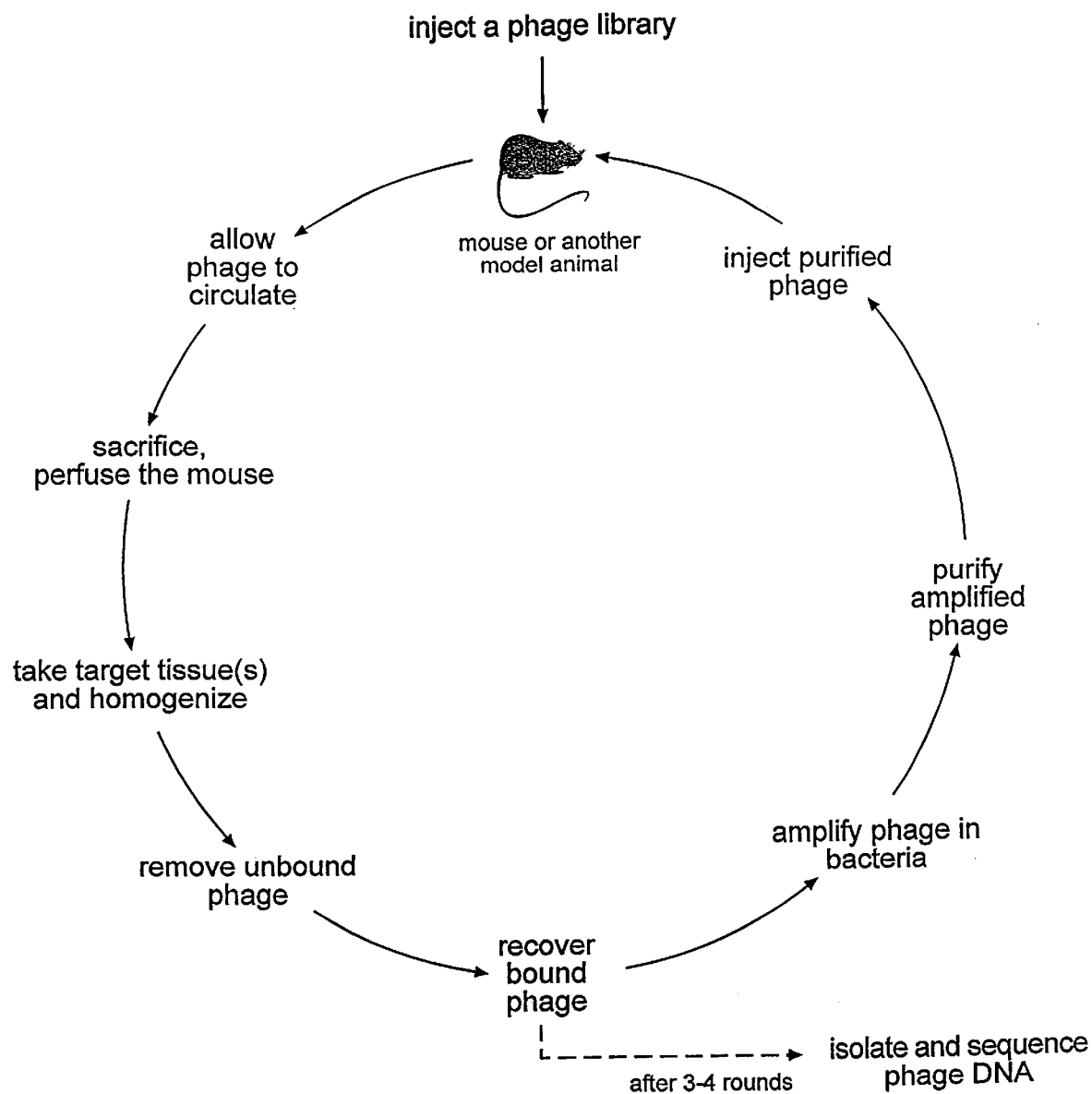
FIG. 1 provides the scheme for selection of tissue-specific phage in vivo.
Figure 2:
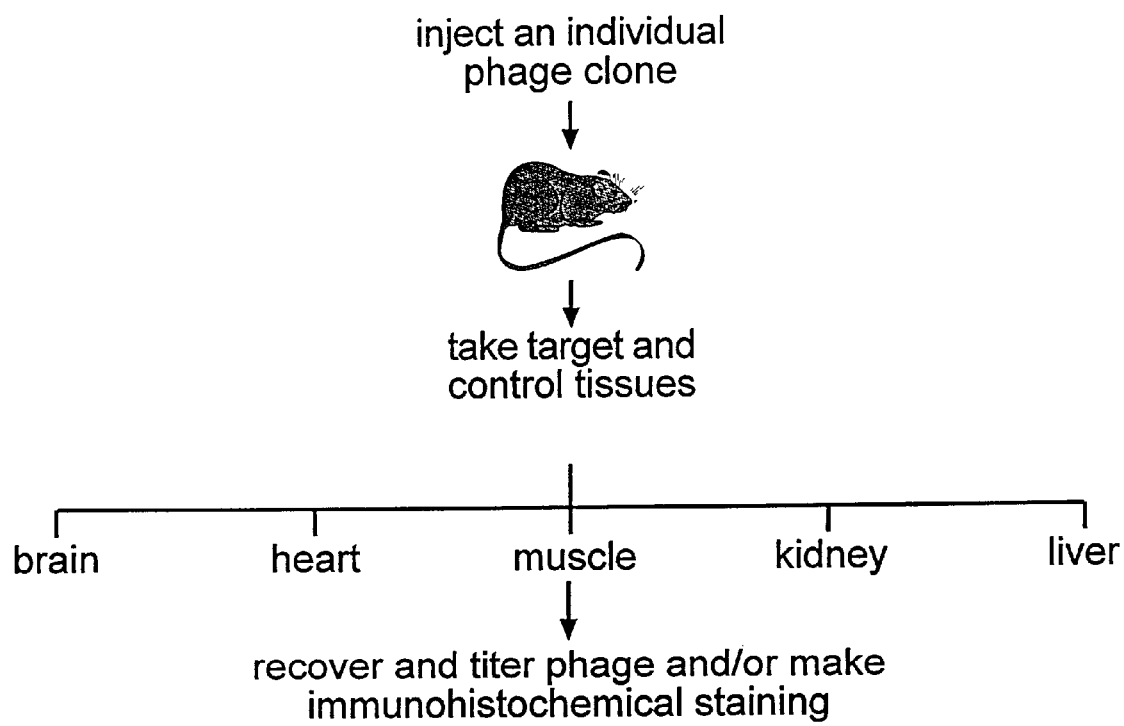
FIG. 2 provides the scheme for demonstrating tissue specificity of selected phage.

The invention is drawn to peptide sequences that are capable of binding central nervous system tissue with high specificity. The peptide sequences are useful for targeting compounds to CNS.

The peptides of the invention are generally short peptide ligands. The peptide ligands exhibit at least three-fold, preferably ten-fold, more preferably greater than ten-fold binding affinity for CNS cells, relative to cells other than CNS cells. The peptides of the invention are able to cross the blood brain barrier (BBB) and bind CNS cells such as neurons, astrocytes, oligodendrocytes, microglia, and the like; as distinguished from endothelial cells of CNS vasculature.

The peptides of the invention are cell-binding and cell-entry peptides. For the most part, the peptides will comprise at least about 5 to about 50 amino acids, preferably at least about 5 to about 30 amino acids, more preferably at least about 7 to about 20 amino acids. It is recognized that consensus sequences may be identified among the peptides that are capable of binding to a target. Such consensus sequences identify key amino acids or patterns of amino acids that are essential for binding. Consensus sequences may be determined from an analysis of peptide patterns that are capable of binding CNS cells. Once recognized, the consensus regions will be used in constructing other peptides for use in targeting the CNS. Such consensus sequences may be tested by constructing peptides and determining the effect of the consensus sequence on binding. In this manner, as long as the consensus sequence is present, the peptide will bind the target.

The peptides can be classified into linear, cyclic and conformational types. While the invention is not bound by any particular mode of action, it is postulated that the shorter peptides, generally from about 7 to about 20 amino acids are involved in linear binding to the target CNS cells. Longer peptides assume conformational folding and are involved in conformational binding. Cyclic peptide structures can also be constructed for use in the invention. In this manner, a core peptide region such as a consensus peptide binding sequence will be flanked with identical sequences to form cyclic peptides. For such construction, libraries are available commercially. See, for example, the Ph.D.™ Phage display peptide library kits from New England Biolabs, Inc. See also, Parmley et al.(1988) *Gene* 73:305–318; Cortese et al.(1995) *Curr. Opin. Biotechnol* 6:73–80; Noren (1996) *NEB Transcript* 8(1):1–5; and Devlin et al.(1990) *Science* 249:404–406.

Peptides of the invention can be determined which are capable of binding any type of CNS cells including neurons, astrocytes, oligodendrocytes, microglia, and the like. Based on the selective binding protocols, peptides which are tissue-type specific or alternatively capable of binding to different CNS cells can be determined. In this manner, peptides can be identified that are specific for binding to, for example, corticospinal systems, subcortical systems, basal ganglia, hippocampus, hypothalamus, pons, and the like.

Certain disorders are known to be associated with particular anatomical systems of the CNS. For example, it is known that tremors and rigidity of Parkinson's Disease, and uncontrollable limb movements of Huntington's chorea are associated with the extrapyramidal system of the limbic system of the brain. Likewise, memory loss associated with Alzheimer's disease is likely to be associated with the hippocampus. Peptides of the invention can be determined which are capable of targeting specific anatomical systems of the CNS for the purpose of treating a disorder associated with that system.

FIG. 3 sets forth amino acid sequences for six peptides which are capable of binding to the brain. Five of the six peptides, LPLTPLP, SSHTISF, LPHQNNR, QPTASLT, and LFTPPVL are specific for binding to the brain; the amino acid sequences for these five peptides set forth in SEQ ID NO:1, SEQ ID NO:2, SEQ ID NO:3, SEQ ID NO:4, and SEQ ID NO:5 respectively. See also Examples 2 and 3. Peptides can also be determined which are specific for binding to more than one organ. For example, the peptide having the amino acid sequence GETRAPL (FIG. 3, Example 2), is capable of binding to skeletal muscle as described in the U.S. Pat. No. 6,329,501; as well as binding to brain as described herein the amino acid sequence for GETRAPL is set forth in SEQ ID NO:6.

In the same manner, the peptides may be species independent. That is, the peptides will bind to the CNS tissue type or anatomical system from any mammalian species. Alternatively, the peptides may be species specific. By species specific is intended that peptides are specific for CNS cells from a particular species and will not bind to CNS cells from another species. Therefore, the peptides may be characterized by tissue specificity, anatomical system specificity, or alternatively by species specificity. Mammalian species of interest include, but are not limited to human, rat, dog, mouse, cat, non-human primate, and the like.

Multiple CNS targets can be utilized to select for CNS-binding peptides. Peptides can be selected against readily available neuronal cell lines from any mammal. Peptides can also be selected against tissue or cell preparations enriched for specific cell types from the CNS of mammals; for example, enriched for neurons and/or astrocytes.

Methods are available in the art for the determination of the peptides of the invention. Such methods include selection from a bacteriophage library which expresses random peptides, mirror image phage display to isolate naturally-occurring L-enantiomers in a peptide library, and the like. See, for example, Barry et al.(1996) *Nature Medicine* 2:299–305; Schumacher et al.(1996) *Science* 271:1854–1857; Pasqualini et al.(1996) *Nature* 380:364–366; and the references cited therein, herein incorporated by reference.

Peptides of the invention can be determined from phage libraries which have been used to select random peptides that bind single proteins. See, Barry et al.(1996) *Nature Medicine* 2:299–305; Devlin et al.(1990) 249:404–406; Cwirla et al.(1990) *Proc. Natl. Acad Sci. USA* 87:6378–6382; and the references cited therein. In this manner, bactriophage libraries can be constructed which display random peptides. These random peptides are expressed as fusion proteins with a phage protein. See, Barry et al.(1996) *Nature Medicine* 2:299–305, herein incorporated by reference. The phage is incubated with the cells of interest, at different temperatures, generally about 4° C. and about 37° C. After repeated selection of phage bound to specific cells, isolated peptides which exhibit a higher affinity for the cells of interest are identified by sequencing. Methods for preparing libraries containing diverse populations are also disclosed in Gordon et al.(1994) *J. Med Chem.* 37:1385–1401; Ecker and Crooke (1995) *BioTechnology* 13:351–360; Goodman and Ro, Peptidomimetics For Drug Design, in "Burger's Medicinal Chemistry and Drug Discovery", Vol. 1, M. E. Wolff (Ed.) John Wiley & Sons 1995, pages 803–861; Blondelle et al.(1995) *Trends Anal. Chem.* 14:83–92; and Sambrook et al., Molecular Cloning: A Laboratory Manual, Cold Spring Harbor Press, 1989. Each of these references are herein incorporated by reference.

Alternatively, or subsequently, to the in vitro binding, the peptides of the invention are selected based on in vivo binding. Such methods for in vivo binding are known in the art. See, for example, Pasqualini et al.(1996) *Nature* 380:364–366; Rajotte et al.(1998) *J. Clin. Invest.* 102:430–437, and the references cited therein for methods of binding to endothelium of tissue vasculature. While the invention is discussed in terms of peptides, it is recognized that other molecules may be identified in the same manner. Such molecules include organic chemicals, modified peptides, proteins such as antibodies, antibody fragments, and the like.

The screening method of the invention comprises administering a library of molecules to the CNS cells of interest and identifying those molecules which are capable of binding. See, for example, U.S. Pat. No. 5,622,699, herein incorporated by reference. Where the library is administered intravenously to a mammalian subject to screen for peptides that bind to the CNS cells of that subject, it is recognized that to cross the blood brain barrier, longer periods of circulation time than four minutes are required. By "circulation time" is intended the elapsed time between administration of the library to the subject and termination of the procedure with respect to a desired organ or tissue by any method including but not limited to sacrificing the animal, freezing the animal, and/or removing the desired tissue (biopsy) from the subject. The optimal circulation time for binding could vary for various peptides, CNS tissue types and anatomical systems. For most peptides, a preferred circulation time is longer than 5 minutes; more preferred is longer than 15 minutes, even more preferred is longer than thirty minutes, and yet even more preferred is sixty minutes or longer.

For peptides capable of binding human CNS cells, non-human primates can be used as the target mammal. Thus, primate species specific peptides can be identified which do not cross react with other mammalian species. For peptides which cross-react or are species independent, after screening in a first mammal, the peptides are screened in at least a second mammal. In this manner, those peptides which bind to more than one species can be determined. Because the mammal is typically sacrificed to determine binding, a non-human primate species can be used for human.

In order to accurately evaluate the affinity of the peptides for their receptors, acoustic wave sensor technology (AWST) is used to evaluate the interaction of the peptide wvith CNS tissue or brain cell preparations, including such preparations enriched for specific cell types. Monolayer films serve as matrices for the immobilization of biotinylated CNS binding peptides via streptavidin. Mass measurements are carried out wvith a microbalance with a mass resolution of 10 nanograms/cm2. A quartz crystal microbalance is calibrated by the deposition of well characterized stearic acid monolayers. The deposition of a single monolayer of the stearic acid onto a TSM crystal adds an additional mass of 2.6×10−7 g/cm2 (for a 38 mNm-1 transfer surface pressure). The microbalance is interfaced with a computer and used as a monitoring device to record the binding of a target protein to the sensor surface when the monolayer with CNS-binding peptides is exposed to tissue homogenates. Peptide-protein interactions are quantified as a change in the resonance frequency of the acoustic wave sensor. The sensor substrate is positioned in the probe arm of the instrument just prior to the delivery of the test solutions. Immediately after recording is started, an aliquot (typically 1 ml) of the control solution is delivered with a pipet to the sensor surface and the voltage is recorded for 4 to 8 minutes. The test solution is carefully removed and a new recording is initiated with an equal aliquot of a solution containing a tissue homogenate. Repeated measurements may be made with the same film.

This AWST technology can be used with tissues and cells from any species, including humans, obtained at autopsy, to both confirm the specificity to the peptides selected in mice to the CNS of that species, and to evaluate subsequent permutations of the consensus peptides for their binding affinity to specific receptors in cells of the central nervous system. For peptides capable of binding human CNS cells, non-human primates can also be used as a target animal to evaluate binding to CNS of a primate species.

The in vivo selection methods of the invention provide methods where selection of peptides which can both cross the blood brain barrier and bind CNS cells can be achieved without specific knowledge of the receptors for the peptides and without having to design specific peptides. Furthermore, the techniques do not depend on use of cultured cells which do not represent differentiation and other characteristics of adult mammalian CNS.

Once peptides have been selected which show an affinity for the target tissue or anatomical system, they may be modified by methods knowvn in the art. Such methods include random mutagenesis, as well as synthesis of the compounds for selected amino acid substitutions. Peptides of various length can be constructed and tested for the effect on binding affinity and specificity. In this manner, the binding affinity may be increased or altered. Thus, peptides may be identified which exhibit specific binding to CNS cells, as well as peptides which exhibit specific binding and internalization by the CNS cells of interest.

The peptides find use in targeting genes, proteins, pharmaceuticals, or other compounds to particular CNS tissue. In this manner, the peptides can be used wvith any vector systems for delivery of specific nucleotides or compositions to the target cells. Nucleotide is intended to encompass gene sequences, DNA, RNA, oligonucleotides, as well as antisense nucleic acids.

The nucleotide sequences encoding the CNS-specific peptides are also encompassed. Where necessary, the nucleotide sequences can be used in the construction of fusion proteins or vectors for use in the invention. Such methods are known in the art. Additionally the construction of expression cassettes are known as well as promoters, terminators, enhancers, etc., necessary for expression.

A number of vector systems are known for the introduction of foreign or native genes into mammalian cells. These include SV40 virus (See, e.g., Okayama et al.(985) *Mol. Cell Biol.* 5:1136–1142); *Bovine papilloma* virus (See, e.g., DiMaio et al.(1982) *Proc. Natl. Acad. Sci. USA* 79:4030–4034); adenovirus (See, e.g., Morin et al.(1987) *Proc. Natl. Acad. Sci. USA* 84:4626; Yifan et al.(1995) *Proc. Natl. Acad. Sci. USA* 92:1401–1405; Yang et al.(1996) *Gene Ther.* 3:137–144; Tripathy et al.(1996) *Nat. Med.* 2:545–550; Quantin et al.(1992) *Proc. Natl. Acad. Sci. USA* 89:2581–2584; Rosenfeld et al.(1991) *Science* 252:431–434; Wagner (1992) *Proc. Natl. Acad. Sci. USA* 89:6099–6103; Curiel et al.(1992) *Human Gene Therapy* 3:147–154; Curiel (1991) *Proc. Natl. Acad. Sci. USA* 88:8850–8854; LeGal LaSalle et al.(1993) *Science* 259:590–599); Kass-Eisler et al.(1993) *Proc. Natl. Acad. Sci. USA* 90:11498–11502); adeno-associated virus (See, e.g., Muzyczka et al.(1994) *J. Clin. Invest.* 94:1351; Xiao et al.(1996) *J. Virol.* 70:8098–8108); herpes simplex virus (See, e.g., Geller et al.(1988) *Science* 241:1667; Huard et al.(1995) *Gene Therapy* 2:385–392; U.S. Pat. No. 5,501, 979); retrovirus-based vectors (See, for example, Curran et al.(1982) *J. Virol.* 44:674–682; Gazit et al.(1986) *J. Virol.* 60:19–28; Miller, A. D. (1992) *Curr. Top. Microbiol. Immunol.* 158:1–24; Cavanaugh et al.(1994) *Proc. Natl. Acad. Sci. USA* 91:7071–7075; Smith et al.(1990) *Mol. Cell. Biol.* 10:3268–3271); herein incorporated by reference.

Standard techniques for the construction of the vectors of the present invention are well-known to those of ordinary skill in the art and can be found in such references as Sambrook et al., *Molecular Cloning: A Laboratory Manual,* 2nd ed. (Cold Spring Harbor, N.Y., 1989). A variety of strategies are available for ligating fragments of DNA, the choice of which depends on the nature of the termini of the DNA fragments and which choices can be readily made by those of skill in the art.

The peptides of the invention can be used with any mammalian expression vector to target the expression system to the appropriate target CNS cells. In this aspect, methods such as those described by Wu et al.(1991) *J. Biol. Chem.* 266:14338–14342; Wu and Wu (1988) *J. Biol Chem.* 263:14621–14624; Wu et al. (1989) *J. Biol. Chem.* 264:16985–16987; Zenke et al.(1990) *Proc. Natl. Acad. Sci. USA* 87:3655–3659; Wagner et al. *Proc. Natl. Acad. Sci.* (1990) 87:3410–3414; can be used.

Where the peptides of the invention are targeting a gene for expression in the CNS, the gene to be expressed will be provided in an expression cassette with the appropriate regulatory elements necessary for expression of the gene.

Such regulatory elements are well known in the art and include promoters, terminators, enhancers, etc.

The peptides of the invention may also be utilized to target liposomes, polylysine, or other polycation conjugates, and synthetic molecules. See, for example, de Haan et al.(1996) *Immunology* 89:488–493; Gorlach et al.(1996) *DTWDTsch Tierarytl Wochenschr,* 103:312–315; Benameur et al.(1995) *J. Phar. Pharmacol.* 47:812–817; Bonanomi et al.(1987) *J. Microencapsul* 4:189–200; Zekorn et al.(1995) *Transplant Proc.* 27:3362–3363.

In this manner, the peptides of the invention can be used to provide therapies for disorders of the CNS including but not limited to epilepsy, Parkinson's disease, Alzheimer's disease, cancers of the CNS, infections of the CNS, schizophrenia, migraine, and the like. That is, genes, proteins, or pharmaceuticals can be directed to the CNS in those patients suffering from the particular disease afflicting the CNS.

More particular embodiments of approaches in which the peptides of the invention can be used to direct substances to the CNS for therapeutic purposes include but are not limited to delivery of genes encoding tyrosine hydroxylase, superoxide dismutase, or glial derived neurotrophic factor for the treatment of Parkinson's disease (Barkats et al., (*Prog Neurobiol* 55: 333–341); delivery of suicide genes, prodrug activating genes, tumor suppressor genes, cytokines mediating anti-tumor responses and antisense DNA to block action of gronvth factors for the treatment of cancers of the CNS including brain tumors(Chung et al.(1998); Surg. Oncol. Clin. N Am 7: 589–602; Maria et al.(1997) *J Child Neurol* 12:77–84). In the same manner, the peptides of the invention may be utilized to target pharmaceuticals and chemotherapeutic agents to treat cancers of the CNS including tumors. Examples of chemotherapeutic agents include methotrexate, adriamycin, cyclophosphamide, and the like. The peptides of the invention can also be utilized to deliver antibiotics for treatment of bacterial infections of the CNS. In this aspect, the peptides of the invention arc particularly useful in situations where the infecting strain is susceptible to a particular antibiotic; however, the antibiotic does not possess the requisite physicochemical properties for crossing the blood brain barrier. The peptides of the invention can also be used to deliver antiviral agents such as nucleotide analogues to the CNS. Further examples of substances which can be targeted to the CNS by the peptides of the invention include the listed neuropharmaceutical agents of U.S. Pat. No. 5,527,527 (column 3, lines 21–65), herein incorporated by reference.

Thus, CNS peptide directed therapies are useful for the treatment of a number of acquired and inherited CNS diseases. Previous gene transfer approaches have been limited by relatively low efficiencies of gene transduction, or by limitations to the mode of administration imposed by the blood brain barrier. The present approach provides a means to increase recombinant gene expression and pharmaceutical concentration in the CNS.

Where it is desired to target substances specifically to more than one organ, the invention provides peptides with binding specificity to more than one organ. In this manner, the peptide having the amino acid sequence GETRAPL (Example 2, SEQ ID NO:6) can be used to target substances to brain and skeletal muscle. Examples of situations in which specific targeting to more than one tissue is desired include targeting of substances for the treatment of diseases which affect more than one organ.

The compositions of the invention may be provided as pharmaceutical formulations suitable for parenteral (e.g., subcutaneous, intradermal, intramuscular, intravenous and intraarticular), oral or inhalation administration. Alternatively, pharmaceutical formulations of the present invention may be suitable for administration to the mucous membranes of the subject (e.g., intranasal administration). It is recognized that intranasal administration could be used to target substances to olfactory neurons, which are otherwise difficult to access. In the same manner, intraocular administration could be used to target substances to the optic nerve. Accordingly, the peptides of the invention could be used to target substances to the optic nerve to treat optic nerve disorders; for example, retinopathics.

Where needed, the pharmaceutical formulations of the present invention may be administered by direct delivery to the central nervous system by intrathecal injection to cerebrospinal fluid or directly into the brain. The formulations may be conveniently prepared in unit dosage form and may be prepared by any of the methods well-knowvn in the art.

Any inert pharmaceutically-acceptable carrier may be used, such as saline, or phosphate-buffered saline, or any such carrier in which the compositions of the present invention have suitable solubility properties for use in the methods of the present invention. Reference is made to Remington's Pharmaceutical Sciences, Merck Publishing Company Easton, P.A., Osol (ed.) (1980) for methods of formulating pharmaceutical compositions.

The peptides of the invention could be used in conjunction with any known methods for delivering substances to the including but not limited to those described in U.S. Pat. No's. 4,866,042; 5,527,527; 5,124,146; 5,672,683; and 5,716,614.

In one embodiment of the methods of the invention, the peptides are utilized in a vector system as the ligand-binding domain for the treatment of CNS disease, particularly Parkinson's disease. The method provides intravenous injection of an expression vector comprising the targeting peptides of the invention operably linked with an expression cassette comprising the tyrosine hydoxylase gene to deliver the tyrosine hydroxylase product to the CNS. Vectors which show efficacy as a gene delivery system for treatment of CNS disorders, including Parkinson's disease are known in the art and could be used as expression vectors in this aspect of the invention. See, for example, Barkats et al., (1998) *Prog Neurobiol* 55:333–341.

The following experiments are offered by way of illustration and not by way of limitation.

EXPERIMENTAL

Example 1

Phage Presentation Libraries May be Utilized to Identify Novel Ligands for Gene Transfer to Brain For therapy of a CNS disorder such as Parkinson's disease, CNS cells need to be targeted. A key factor in any targeting scheme is the availability of appropriate specific molecules on the target cells which can be exploited for targeting. Available ligands for targeting the CNS are limited in number and functional applicability. Systems which, while utilizing a variety of different approaches, fundamentally share the similarity of examining libraries of peptides for their ability to bind to specific cell types, specially in vivo, are useful for determining ligands for targeting the CNS. Advantages of such systems include the following:

a. Unlike the use of known ligands, the process requires no prior knowledge of the biology of the target cells.

b. Molecular recognition and selection are not influenced by the immunogenicity of candidate targets.

c. As a result, peptide ligands should be more easily isolated and incorporated into biological vectors by cloning or by chemical conjugation to synthetic vectors.

Example 2

Selection of Peptides Against CNS

FIG. 1 provides the scheme for selection of tissue specific phage in vivo. In this example, candidate brain-binding peptides were selected by panning in BALB/c mice. In round one of selection, the phage library was injected intravenously. After thirty minutes of circulation, the mice were euthanized by carbon dioxide inhalation, perfused with 60 ml of ice cold PBS via the left ventricle, and brain tissue was recovered from the animals. The tissue was minced into small pieces and rinsed repeated in PBS, followed by homogenization in lysis buffer. The tissue homogenate was then incubated with fresh E coli cells and the phage present allowed to infect and lyse the bacteria. Phage were recovered by polyethylene glycol precipitation of the lysate. In subsequent rounds, the phage purified from brain tissues recovered in the previous round was injected intravenously, and tissue was recovered after thirty to sixty minutes of circulation. After the last round, the phages were plated on a lawn of bacteria and a number of pliage plaques were isolated and the DNA sequenced. Of these, a certain percentage represented the dominant selected clone.

Therefore, tissue-specific peptides were identified which bind to, and may be internalized by brain cells. Specific peptides sequences included:

GETRAPL (Gly-Glu-Thr-Arg-Ala-Pro-Leu, SEQ ID NO:6) Note: This peptide also binds skeletal muscle. See U.S. Pat. No. 6,329,501.

LPLTPLP (Leu-Pro-Leu-Thr-Pro-Leu-Pro, SEQ ID NO:1)

SSHTISF (Ser-Ser-His-Thr-Ile-Ser-Phe, SEO ID NO:2)

The experiments disclosed herein, represent the first in vivo selection of peptides that cross the BBB and bind brain tissue in any species. Generally, phage was left to circulate for thirty minutes to one hour. All three peptides (listed above) were selected after four rounds.

Specific binding to brain tissue and the ability of the peptides to cross the blood brain barrier is further assessed by administering fluorescent label-conjugated peptides under the conditions described above, and sectioning the brain according to methods known in the art. Location of the peptides are determined by techniques known in the art including but not limited to laser confocal microscopy, fluorescent microscopy, autoradiography, and the like.

The frequency of appearance of each amino acid within the library is known. Thus, the frequency of amino acids within the pool of selected peptides can be compared. A number of amino acids can be observed to be over-represented and may be significant for brain binding. Such amino acids may play a role in consensus sequences that are important for binding. One of skill in the art may identify consensus sequences by analysis as well as construction of synthetic sequences and testing binding.

Example 3

Selection of a Panel of Brain-Binding Peptides

To remove unbound, non-specific phage, from the parenchyma of the tissue, the screening protocol of Example 2 was modified. After intravenous administration, the phage were left in circulation for 1 hour (30 minutes in Example 2) to allow more phage clones with CNS binding affinity to reach their target. CNS tissue samples were then homogenized in TBS buffer instead of the lysis buffer which was used at this step previously. Tissue homogenates were pelleted by centrifugation and the supernatant was discarded. The pellet was washed two more times in TBS to remove unbound phage. The pellet was re-homogenized in lysis buffer and the remainder of the selection protocol was completed as described in Example 2. The following brain specific peptides were determined:

LPHQNNR (Leu-Pro-His-Gln-Asn-Asn-Arg, SEQ ID NO:3)

QPTASLT (Gln-Pro-Thr-Ala-Ser-Leu-Thr, SEQ ID NO:4)

LFTPPVL (Leu-Phe-Thr-Pro-Pro-Val-Leu, SEQ ID NO:5)

Example 4

Identification of Peptide Target Ligands

Peptides identified in Examples 2 and 3 are used to detect the cellular protein target to which they bind. Detection of the target protein is performed in a crude protein lysate which is prepared by solubilization of cell membranes in a buffer containing 2% Triton X-100 as a detergent. Proteins are fractionated by SDS electrophoresis in a polyacrylamide gel and transferred to a nitrocellulose membrane. Peptide ligands are synthesized, labeled with biotin and HPLC purified to 98%. The membranes are hybridized with the labeled peptide and the bound peptide is detected with a reagent such as streptavidin conjugated to alkaline phosphatase and visualized after incubation in a colorogenic substrate for alkaline phosphatase (e.g. BCIP/NBT). Direct visualization allows the mass of the target protein to be deduced.

Proteins isolated by the technique described above are further analyzed and subjected to polypeptide fragment sequencing. Peptide sequencing is readily available from commercial sources. The peptide sequences are compared to known sequences in the translated GenBank and SwissPro protein sequence databases to identify the protein. If no homologies are found, the sequences determined from the peptide fragments are used to synthesize degenerate oligonucleotides. These oligonucleotides are used under standard Reverse Transcriptase Polymerase Chain Reaction (RT-PCR) conditions to amplify the cDNA of the putative receptor for DNA sequencing. Once identified, the protein is cloned, expressed in an appropriate system such as baculovirus/SF-9 cells, and is used directly in biochemical assays to measure the binding affinity of the peptide for the target protein. Additionally, permutations of the consensus peptide sequence are used to further elucidate the optimal peptide for binding to the target protein.

Example 5

Therapy in an Animal Model i. Pre-treatment Studies

Neonatal rat models of Parkinson's disease deficient in tyrosine hydroxylase (TH) (1 day to 1 week old) are tested for the enzymes's deficiency using a PCR-based test. Homozygous mutants for TH deficiency are used in this study. Brain biopsies are taken from representative rats from the population. Portions of these biopsies arc frozen and evaluated histochemically. Tissue samples are homogenized and assayed for TH activity. Whole blood and brain samples are frozen at −70° C. to provide pre-treatment controls for Southern hybridizations, PCR amplification of vector sequences, TH activity studies, and TH-specific immunoblots. Serum samples are frozen as controls for the antigenicity studies described below.

ii. In vivo Gene Delivery to TH Deficient Rats

After completion of the pre-treatment studies, each rat is sedated, and an intravenous catheter placed in the tail vein. Tropism-modified vectors comprising the peptides and expression cassettes containing TH are delivered as a slow injection. During injection, the rats are monitored for signs associated with adverse reactions such as anaphylaxis, and should such reactions occur, administration of the vector is suspended and appropriate treatments initiated.

iii. Studies to Detect the Transferred Rat TH cDNA

Brain biopsies are taken from representative animals at one, two, three, four, six and eight weeks following the injection of the vector, and monthly thereafter. DNA is recovered from this tissue sample and examined by PCR for the transferred gene.

iv. Immunological Detection of Tissue Specific Expression of TH

To determine if the vector which has been transferred to the brain is expressing TH, TH specific immunoblots are performed. One hundred to one hundred fifty micrograms of protein are loaded into each well of a 7.5% polyacrylamide gel. Following electrophoresis the gel is stained with coomassie brilliant blue to show protein content, and the electrophoretically transferred to 0.45 micron nitrocellulose membranes. The membranes are blocked with 5% milk powder for 1 hr, followed by 0.05% Tween 20 for 30 min. The membranes are then incubated with the anti-TH primary antibody for 18 hr at room temperature, with gentle agitation. Three washes with Tris-buffered saline (150 mM Tris, 10 mM NaCl, pH 7.5; TBS), 30 seconds to one minute each, are followed by a 3 hr incubation with peroxidase-conjugated secondary antibody (Sigma), at room temperature. A final three rinses in TBS arc followed by the addition of 4 chloro-naphthol to allow for color development.

v. Biochemical Detection of Enzyme Activity from Transferred TH

To determine if the expressed TH possesses enzymatic activity, the CNS biopsy samples are evaluated by biochemical assay.

vi. Histochemical Localization of Tissue-specific Expression of TH

Determination of the number and type of CNS cells expressing TH activity is performed by histochemical staining for TH. Briefly, small pieces of brain, frozen in liquid nitrogen-cooled isopentane, are mounted in a cryostat and sectioned at 6 microns. These sections are placed on microscope slides, dried, and incubated in a TH assay solution containing a label-conjugated substrate. The present of TH activity is seen as a detectable stain within the cells.

Example 6

Targeting of Fluorescent Microspheres to Brain Tissue

To determine the size of particle which may access the brain, a series of different sized, fluorescently labeled, microspheres are cross linked to the brain targeting peptides. These microspheres are injected intravenously and allowed to circulate for up to one hour before the mouse is euthanized and perfused. The efficiency of targeting to brain, and the size cutoff of targeted microspheres are analyzed using fluorescent microscopy.

Example 7

Targeting an Active Pharmaceutical to Brain

Brain targeting peptides are coupled to the neurologically active compound phenobarbital by cross linking. Neurological activity is monitored in both mice and rats given the peptide-conjugated drug intravenously. Dose response curves for phenobarbital and phenobarbital-peptide are compared to determine if the peptide ligand is used to lower the administered dose of drug, while achieving the same pharmacologic effect.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated brain-specific peptide capable of binding to brain cells in vivo, wherein said peptide consists of the amino acid sequence set forth in SEQ ID NO:1.

2. An isolated peptide consisting of the amino acid sequence set forth in SEQ ID NO:1 coupled to a compound.

3. The peptide of claim 2, wherein said compound is selected from the group consisting of drugs, proteins, and nucleic acids.

4. The peptide of claim 2, wherein said compound is useful for treating a brain disorder.

* * * * *